US007256891B2

(12) United States Patent
Domack et al.

(10) Patent No.: US 7,256,891 B2
(45) Date of Patent: Aug. 14, 2007

(54) SENSOR ALIGNMENT APPARATUS FOR AN ANALYSIS SYSTEM

(75) Inventors: Thomas E. Domack, Miami, FL (US); Santos E. Vargas, Miami Lakes, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 201 days.

(21) Appl. No.: 10/923,974

(22) Filed: Aug. 23, 2004

(65) Prior Publication Data

US 2006/0038989 A1 Feb. 23, 2006

(51) Int. Cl.

| | |
|---|---|
| ***G01B 11/00*** | (2006.01) |
| ***G01N 33/48*** | (2006.01) |
| ***G01N 21/00*** | (2006.01) |
| ***G01N 15/02*** | (2006.01) |
| ***A47B 11/00*** | (2006.01) |
| ***A47B 9/00*** | (2006.01) |
| ***F16M 13/00*** | (2006.01) |
| ***F16M 11/00*** | (2006.01) |

(52) U.S. Cl. .......................... 356/400; 356/39; 356/73; 356/335; 356/337; 108/137; 108/138; 108/144.11; 248/124.1; 248/157; 248/176.1; 248/424; 248/913

(58) Field of Classification Search ..................... None
See application file for complete search history.

(56) References Cited

U.S. PATENT DOCUMENTS 4,333,044 A * 6/1982 Blitchington ............... 318/636
4,409,860 A * 10/1983 Moriyama et al. ....... 74/490.09
4,723,086 A * 2/1988 Leibovich et al. .......... 310/328
5,020,357 A * 6/1991 Kovacevic et al. .......... 73/1.15
5,040,059 A * 8/1991 Leberl ........................ 348/135
5,093,234 A * 3/1992 Schwartz ................... 435/7.21
5,125,737 A 6/1992 Rodriguez et al.
5,135,302 A * 8/1992 Hirako ........................ 356/73
5,323,012 A * 6/1994 Auslander et al. ....... 250/492.2
5,453,840 A * 9/1995 Parker et al. .............. 356/400
5,629,765 A * 5/1997 Schmutz .................... 356/121

(Continued)

*Primary Examiner*—Gregory J. Toatley, Jr.
*Assistant Examiner*—Gordon J. Stock, Jr.
(74) *Attorney, Agent, or Firm*—Maginot, Moore & Beck; Mitchell E. Alter

(57) ABSTRACT

An apparatus for analyzing a population of particles is set forth. The apparatus includes an emitter adapted to generate a beam of electromagnetic radiation, such as from a laser, and a particle chamber disposed in a path of the electromagnetic radiation beam. The apparatus also includes a sensor to detect electromagnetic radiation scattered by or otherwise received from the particle chamber. A sensor alignment unit supports the sensor along a detection axis and allows adjustment of the position of the sensor along orthogonal axes lying in a plane that is generally perpendicular to the detection axis. In one embodiment, the sensor alignment unit includes a first support platform and a first adjustment mechanism disposed to adjust the position of the first support platform along a first orthogonal axis. The sensor alignment unit also includes a second support platform that supports the sensor. The second support platform is connected to the first support platform in such a manner as to allow the second support platform to move along a second orthogonal axis. A second adjustment mechanism is provided to adjust the position of the second support platform with respect to the first support platform along the second orthogonal axis. In this manner, the position of the sensor can be adjusted to optimize detection of the desired particle characteristics.

48 Claims, 5 Drawing Sheets

U.S. PATENT DOCUMENTS 5,675,517 A * 10/1997 Stokdijk .................. 702/85
6,417,920 B1 * 7/2002 Shimaoka .................. 356/336
6,456,375 B1 * 9/2002 Ottens et al. .............. 356/339
6,532,069 B1 * 3/2003 Otsuki et al. .............. 356/338
6,784,981 B1 * 8/2004 Roche et al. ................ 356/39
6,873,420 B2 * 3/2005 Davis et al. ................ 356/601
6,954,262 B2 * 10/2005 Buzzetti .................. 356/73.1

* cited by examiner

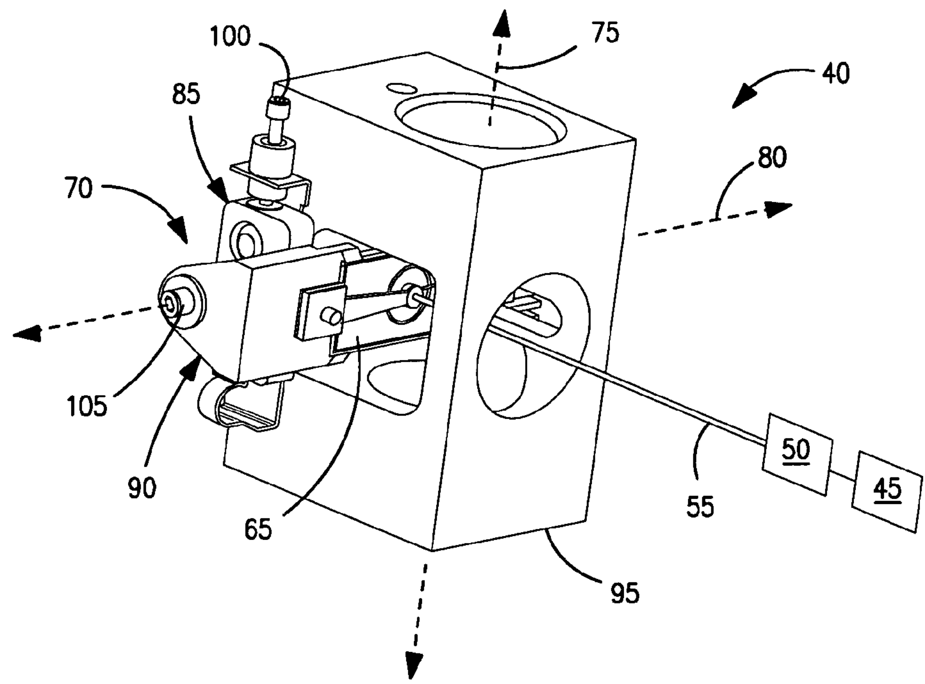
FIG. 2A
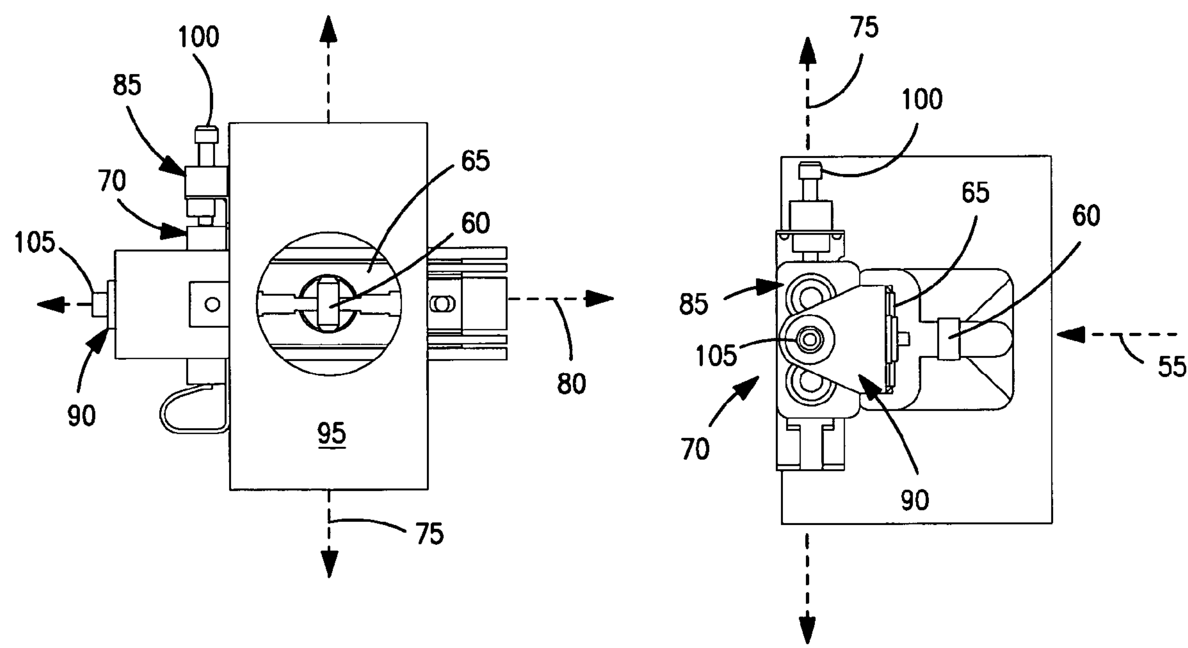
FIG. 2B
FIG. 2C

SENSOR ALIGNMENT APPARATUS FOR AN ANALYSIS SYSTEM

FIELD OF THE INVENTION

The present invention is generally directed to a sensor alignment apparatus for use in an analysis system. More particularly, a sensor alignment apparatus that supports and positions an optical detector along an electromagnetic beam detection path in a flow cytometer is set forth.

BACKGROUND OF THE INVENTION

Apparatus that are designed to measure one or more characteristics of a population of particles, such as biological cells, have become quite common in laboratory environments. Such apparatus are available for analyzing a wide range of particle types using a variety of different analysis methods. For example, data relating to a particular cellular characteristic may be acquired through direct observation of treated biological cell populations. This method is frequently used to diagnose hematological anomalies and diseases. Another type of analysis system that acquires biological and/or chemical data in an indirect manner employs a population of man-made particles. Generally stated, the prefabricated particles are in the form of spheres. The spheres include non-reactive cores having reactive surface coatings. The surface coatings are chosen to react with a target chemical constituent of an analyte in a known manner to thereby alter the characteristic, such as fluorescence, of the spheres. The spheres are introduced to an analyte and the resulting reaction (or failure to react) is detected by the analysis system.

U.S. Pat. No. 5,125,737, to Rodriguez et al. describes a flow cytometer in which a stream of particles is passed into and through a point focused beam of electromagnetic radiated energy. The '737 patent is incorporated herein by reference. One embodiment of the apparatus is shown in FIG. 1. The apparatus comprises an elongated, cylindrical member, forming a flow cell 10. The flow cell 10 can be formed from any optically transparent material, for example, fused silica, quartz, or sapphire. The interior portion of the flow cell 10 is cylindrical throughout its length, except for a narrowed or necked-down aperture 12 through which a biological cell sample is passed as a focused stream 14. The exterior walls 15 of the flow cell 10 are cylindrical and include an optical flat 16. A lens system 18 focuses a beam 20 of electromagnetic energy, preferably from a laser 22, into a spot at the aperture 12. A photodetector assembly 24, acting as a scattered radiation receptor, is positioned in a plane orthogonal to and centered on the commission axis 26 of the laser radiated electromagnetic energy.

The photodetector assembly 24 is comprised of an electromagnetic sensor 25 with a mask 28 and a beam dump 30 (an obstruction for removing unwanted laser light). The mask 28 can be of a circular, elliptical, or other shape, as required to obtain equivalent light scattering information from flow cells 10 of different architectures. The mask is oriented coaxial with the laser light beam 20. The beam dump 30 extends horizontally across the photodetector assembly 24 facing the laser beam as shown. The beam dump 30 can be slightly angularly fanned out from the center to provide a cleaner signal-to-noise output.

In operation, electromagnetic radiation emitted by laser 22 passes through the lens system 18 and, therefrom, through the particle stream passing through flow cell 10. The electromagnetic radiation is scattered by the particles of the stream 14 into a plurality of beams 32. The magnitudes of the beams 32 at various scattering angles are detected by the photodetector assembly 24. Photodetector assembly 24, in turn, provides electronic signals corresponding to the magnitudes of the beams 32 to subsequent electronic circuits for further processing, conversion and data analysis.

The position of the photodetector assembly 24 with respect to the other elements of the apparatus has now been found to be an important aspect of the overall accuracy of the foregoing system. Until now, the accurate positioning of the photodetector assembly 24 has been achieved using fixed sensor support frames that are manufactured to extremely tight tolerances. Such tight manufacturing tolerances are both costly and sometimes difficult to achieve. Accordingly, an alternative to this fixed sensor support approach is desirable.

SUMMARY OF THE INVENTION

An apparatus for analyzing a population of particles is set forth. The apparatus includes an emitter adapted to generate a beam of electromagnetic radiation, such as from a laser, and a particle chamber disposed in a path of the electromagnetic radiation beam. The apparatus also includes a sensor to detect electromagnetic radiation scattered by or otherwise received from the particle chamber. A sensor alignment unit supports the sensor along a detection axis and allows adjustment of the position of the sensor along orthogonal axes lying in a plane that is generally perpendicular to the detection axis. In one embodiment, the sensor alignment unit includes a first support platform and a first adjustment mechanism disposed to adjust the position of the first support platform along a first orthogonal axis. The sensor alignment unit also includes a second support platform that supports the sensor. The second support platform is connected to the first support platform in such a manner as to allow the second support platform to move along a second orthogonal axis. A second adjustment mechanism is provided to adjust the position of the second support platform with respect to the first support platform along the second orthogonal axis. In this manner, the position of the sensor can be adjusted to optimize detection of the desired particle characteristics.

BRIEF DESCRIPTION OF THE DRAWINGS

FIGS. 2A through 2C are schematic representations of one embodiment of a flow cytometer constructed in accordance with the teachings of the present invention.

DESCRIPTION OF A PREFERRED EMBODIMENT OF THE INVENTION

Figure 1:
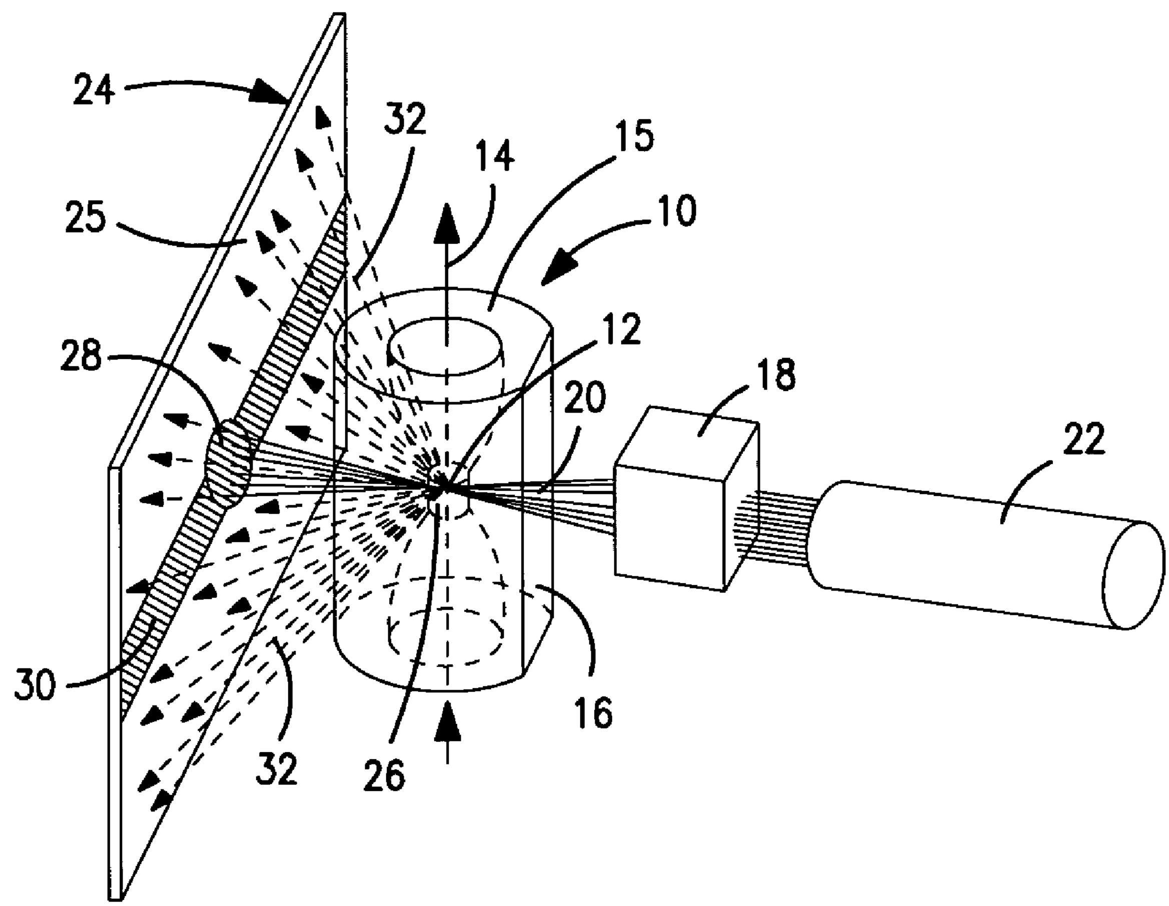
FIG. 1 is a schematic representation of a flow cytometer constructed in accordance with teachings of the prior art.

FIGS. 2A through 2C illustrate one embodiment of an apparatus for analyzing a population of particles, shown generally at 40. Some components of the apparatus 40 are similar to the corresponding components found in the apparatus shown in U.S. Pat. No. 5,125,737, to Rodriguez et al., set forth above. To this end, apparatus 40 includes an electromagnetic emitter 45 and focusing system 50. The electromagnetic emitter 45 and focusing system 50 are adapted to direct a beam of electromagnetic radiation along an emission axis 55. A particle chamber 60 is disposed along the emission axis 55 between the focusing system 50 and a sensor 65. Particles flowing through particle chamber 60 influence the electromagnetic radiation provided along the emission axis 55. Sensor 65 is adapted to detect electromagnetic radiation at one or more wavelengths in the electromagnetic spectrum. The wavelengths, for example, may correspond directly to the wavelengths of the electromagnetic radiation generated by the emitter 45 or, alternatively, may correspond to wavelengths of fluorescent emissions generated by the particles under analysis as they flow through the particle chamber 60. The electromagnetic radiation received by sensor 65 is provided from the particle chamber 60 along a detection axis. In the illustrated embodiment, the detection axis and emission axis 55 are the same.

Unlike prior apparatus that support sensor 65 in an absolute fixed relationship with the apparatus frame (and, thus, in an absolute fixed relationship with the detection axis 55), the sensor 65 of apparatus 40 is fixed to a sensor alignment unit 70. The sensor alignment unit 70 is adapted to allow adjustment of the position of the sensor 65 along orthogonal axes 75 and 80 that lie in a plane that is generally perpendicular to the detection axis 55.

In the illustrated embodiment, the sensor alignment unit 70 includes a vertical adjustment assembly 85 and a horizontal adjustment assembly 90. Vertical adjustment assembly 85 is supported by a fixed frame member 95 and is provided with an adjustment screw 100 that allows the position of the sensor 65 to be adjusted along the vertical axis 75. Horizontal adjustment assembly 90 is supported by the vertical adjustment assembly 85 and is provided with a further adjustment screw 105 that allows the position of the sensor 65 to be adjusted along the horizontal axis 80.

Figure 3A:
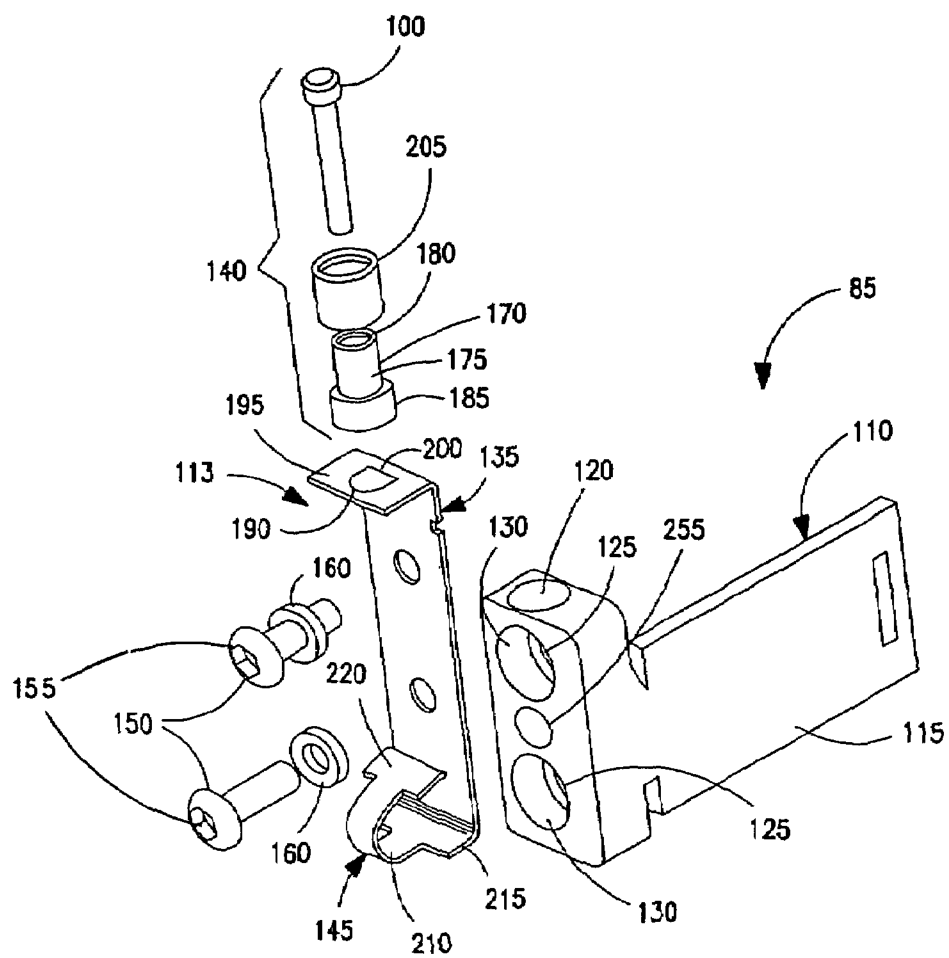
FIGS. 3A through 3C are schematic representations of one embodiment of a vertical adjustment assembly suitable for use in adjusting the vertical position of the sensor in the flow cytometer shown in FIGS. 2A through 2C.
Figure 3B:
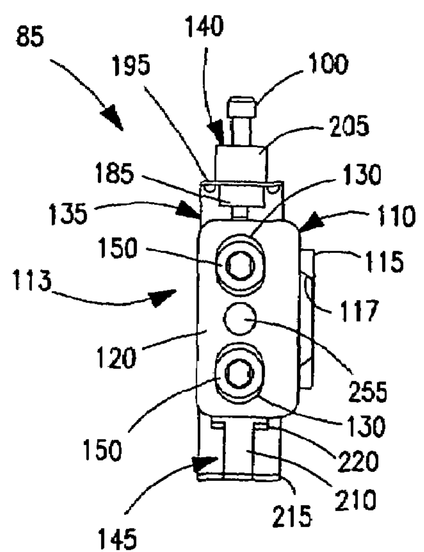
Figure 3C:
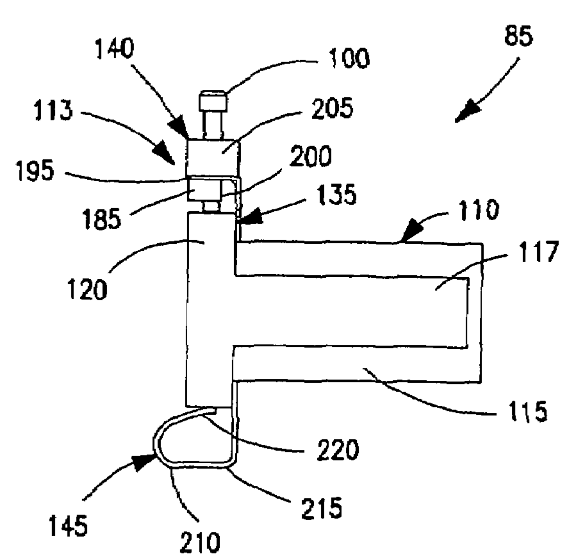

The particular elements forming the vertical adjustment assembly 85 are illustrated in FIGS. 3A through 3C. Generally stated, the vertical adjustment assembly 85 of the illustrated embodiment includes a support platform 110 and an adjustment mechanism 113. The support platform 110 includes a mounting base 115 having a channel 117 to which the horizontal adjustment assembly 90 is attached. A connection shoulder 120 extends at a right angle from the end of the base 115. One or more bores 125 proceed through connection shoulder 120. Each bore 125 includes a corresponding counterbore 130.

Adjustment mechanism 113 includes a bracket 135 having a screw drive 140 disposed at a first end thereof and a return spring 145 disposed at a second end thereof. A pair of securements 150 extends through bores 125 to attach the bracket 135 to frame member 95. Bores 125 and securements 150 are dimensioned to allow vertical movement of the connection shoulder 120 along bores 125, in effect allowing bores 125 to function as guide slots for vertical movement of the support platform 110. In the illustrated embodiment, the securements 150 are in the form of screws 155 that extend through respective plastic washer bearings 160.

The vertical position of the connection shoulder 120 and, thus, support platform 110, along axis 75 is principally constrained between the maximum upper and lower positions by the screw drive 140 and return spring 145. Screw drive 140 includes a fine resolution screw 100 that engages a corresponding threaded insert assembly. The threaded insert assembly comprises a fine resolution threaded base 170. Base 170, in turn, is comprised of a body portion 175 having a centrally disposed threaded aperture 180 and a flange 185. The body portion 175 extends through the bottom of an aperture 190 in a shoulder 195 of bracket 135. Both the body portion 175 and aperture 190 include flats 200 to prevent rotation of the body portion 175 when it is positioned within aperture 190. A nut 205 engages threads at the exterior surface of body portion 175 to secure base 170 within aperture 190. Fine resolution screw 100 extends through the base 170 to engage a first side of the connection shoulder 120.

Return spring 145 is formed from a U-shaped extension of bracket 135. The U-shaped extension includes a narrowed strip 210 of material extending from a lip 215 at the bottom of bracket 135 that curves around and terminates at a widened support section 220. Support section 220 engages a second side of the connection shoulder 120 opposite adjustment screw 100.

In operation, return spring 145 is compressed to provide a biasing force against the bottom of the connection shoulder 120 in the direction of the screw drive 140. The position of the shoulder 120 along the vertical axis 75 is principally controlled by adjusting the degree to which the fine resolution screw 100 extends through the base 170 and into contact with the upper portion of shoulder 120.

FIGS. 4A through 4E illustrate one embodiment of a horizontal adjustment assembly 90 and its corresponding relationship to the support platform 110 of the vertical adjustment assembly 85. Generally stated, the horizontal adjustment assembly 90 is comprised of a sensor support platform 210 and a screw drive 215. The sensor support platform 210 includes a front face 220 that is adapted to connect to the sensor 65. Guide channels 225 may be provided in the face 220 to hold the signal/power wires used by the sensor 65. Various other structures may be provided on the front face 220 to adapt it for support of the particular sensor design.

Figure 4A:
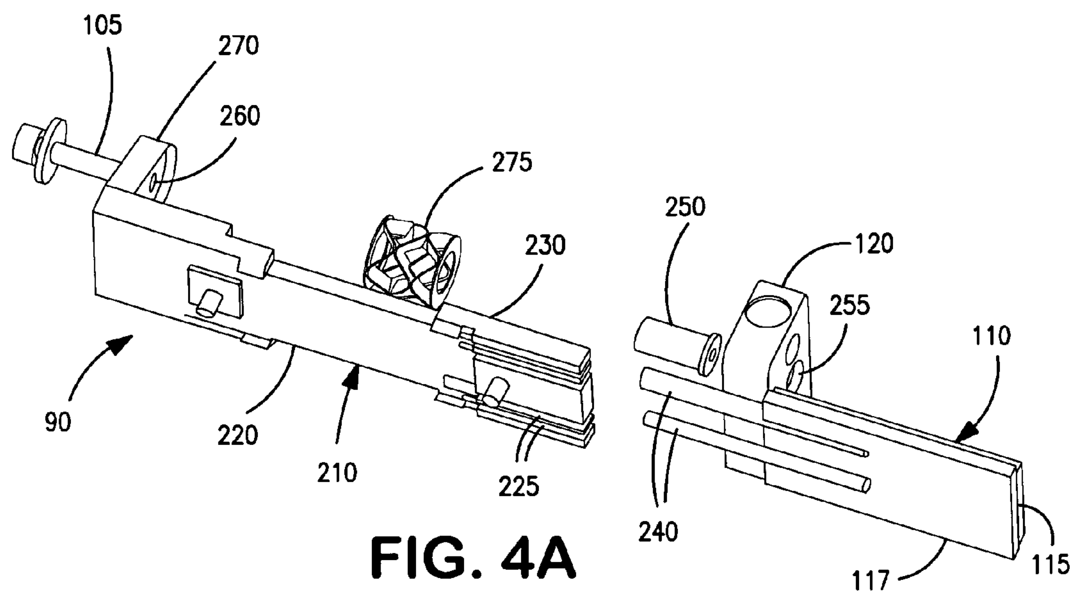
FIGS. 4A through 4E are schematic representations of one embodiment of a horizontal adjustment assembly suitable for use in adjusting the horizontal position of the sensor in the flow cytometer shown in FIGS. 2A through 2C.
Figure 4B:
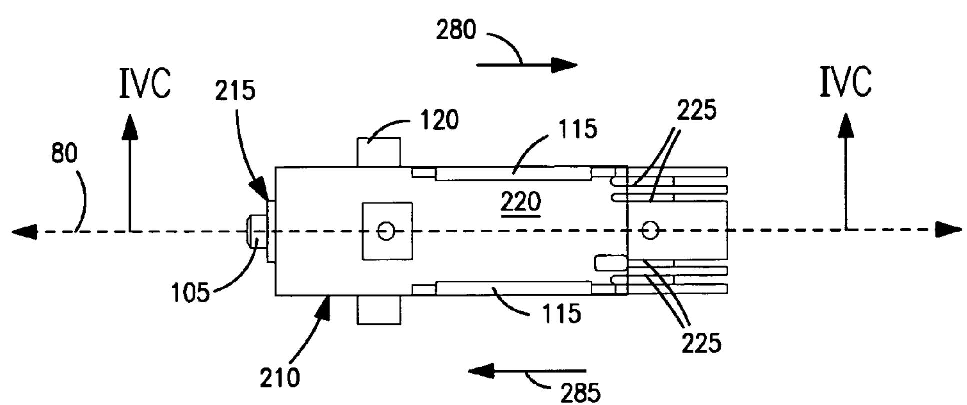
Figure 4C:
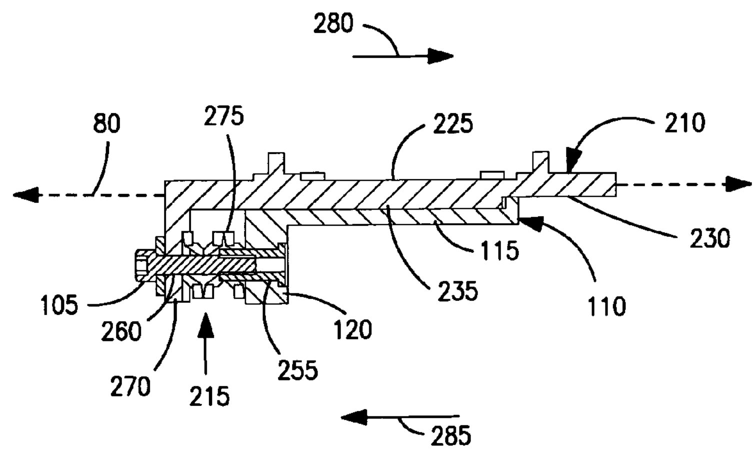
Figure 4D:
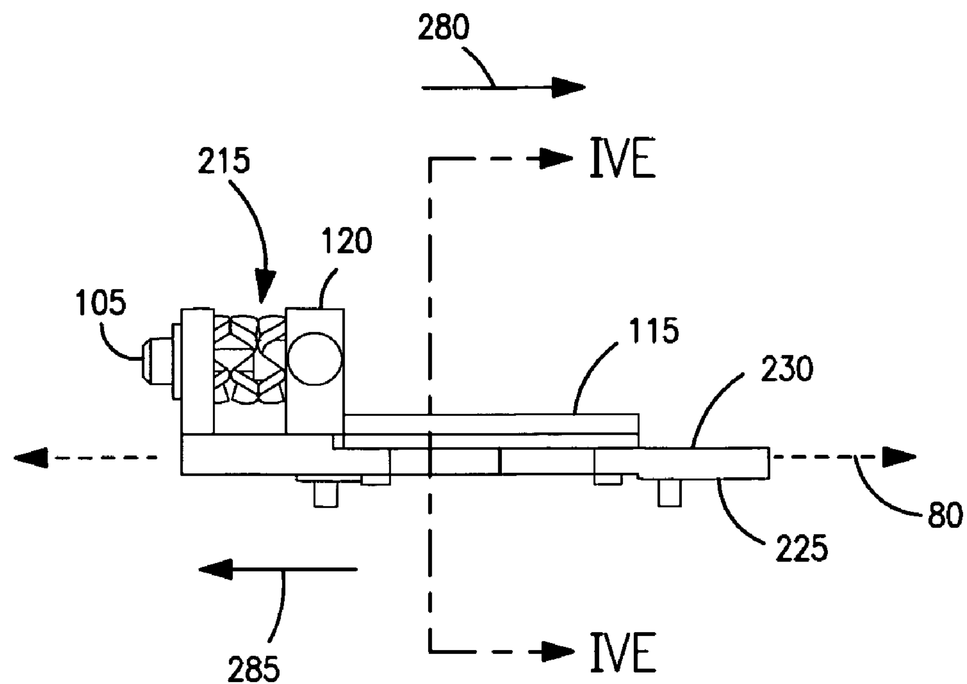
Figure 4E:
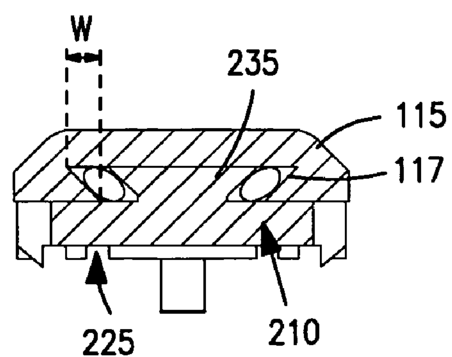

As shown in FIGS. 4D and 4E, the rear surface 230 of sensor support platform 210 includes a dovetail extension 235 that engages the channel 117 at the front face of mounting base 115. Together, extension 235 and channel 117 form a generally T-shaped slot connection that allows the sensor support platform 210 to move with respect to the mounting base 115 along horizontal axis 80. Teflon tube bearings 240 are disposed between the interior corners of dovetail extension 235 and the interior surface of channel 117. Tube bearings 240 have a naturally cylindrical cross-section. However, the dimensions of the tube bearings 240 are preferably chosen so that the bearings deform from their cylindrical cross-sectional shape to the generally square cross-sectional shape shown in FIG. 4E when the extension 235 is engaged with the channel 117. To this end, the exterior diameter of each tube bearing 240 is approximately 1.15 times the size of the dimension W of the dovetailed portion of channel 117. Other materials and diameters may also be used so long as the bearing arrangement provides a sufficient amount of friction to lock the sensor support platform 210 into position with the mounting base 115 while concurrently allowing movement of the sensor support platform 210 along the horizontal axis 80. Bearings 240 perform several functions, including acting as compensators that facilitate the use of T-slot connections manufactured to various tolerances.

One embodiment of the screw drive 215 of the horizontal adjustment assembly 90 is particularly shown in FIGS. 4A, 4C and 4D. As illustrated, screw drive 215 includes a threaded insert 250 that extends through an aperture 255 in the connection shoulder 120 of support platform 110. The fine resolution adjustment screw 105 extends through an aperture 260 in shoulder 270 of sensor support platform 210 to engage the threaded insert 250. A return spring 275 provides a tension force along the horizontal axis 80 to drive shoulders 120 and 270 apart.

In operation, the horizontal position of the support platform 210 (and, thus, the horizontal position of the sensor 60) is set by turning adjustment screw 105 until the desired position has been obtained. When the adjustment screw 105 is turned so that it is driven into the threaded insert 250, shoulder 270 is driven toward shoulder 120 against the bias of return spring 275. As such, sensor support platform 210 is driven in the direction of arrow 280 with respect to support platform 110 as shown in FIGS. 4B, 4D and 4E. When the adjustment screw 105 is turned so that it is gradually removed from the threaded insert 250, shoulder 270 is driven away from shoulder 120 by the forces generated by return spring 275. As such, sensor support platform 210 is driven in the direction of arrow 285 with respect to support platform 110 as shown in FIGS. 4B, 4D and 4E.

Placement of the sensor 65 at the optimal sensing position can be achieved by monitoring the output of the sensor 65 while concurrently operating the foregoing adjustment mechanisms. For example, a signal detector, such as an oscilloscope, may be connected to detect the output signal from the sensor 65 while a stream of particles flow through particle chamber 60. Each particle or group of particles flowing through the particle chamber 60 generates a corresponding output signal from the sensor 65 that can be visually monitored on the oscilloscope. The horizontal sweep frequency of the oscilloscope can be set to generally the same or some multiple of the frequency at which the particles flow through the particle chamber 65. This synchronization results in the generation of a pulse peak or minimum at regular intervals along the horizontal axis of the oscilloscope. The vertical adjustment assembly 85 and horizontal adjustment assembly 90 are then operated until the output signal (i.e., the pulse peak or pulse minimum) from the sensor 65 reaches its maximum magnitude thereby indicating optimal positioning of the sensor 65 with respect to the detection axis 55. Other means for determining the optimal position of the sensor 65 are likewise suitable.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. An apparatus for analyzing a population of particles comprising:

(a) an emitter adapted to generate a beam of electromagnetic radiation;

(b) a particle chamber disposed in a path of said beam of electromagnetic radiation;

(c) a sensor adapted to detect electromagnetic radiation; and (d) a sensor alignment unit supporting said sensor along a detection axis, said sensor alignment unit adapted to allow adjustment of the position of said sensor along at least two orthogonal axes lying in a plane that is generally perpendicular to said detection axis, wherein said sensor alignment unit comprises:

a first support platform;

a first adjustment mechanism disposed to adjust the position of said first support platform along a first axis of said orthogonal axes;

a second support platform connected to said first support platform and supporting said sensor;

a second adjustment mechanism disposed to adjust the position of said second support platform with respect to said first support platform along a second axis of said orthogonal axes.

2. An apparatus as claimed in claim 1 wherein said particle chamber is a flow cell of a flow cytometer.

3. An apparatus as claimed in claim 1 wherein said sensor is an optical sensor.

4. An apparatus as claimed in claim 1 wherein said first support platform comprises:

a support base; and a connection shoulder extending from said support base, said connection shoulder having at least one guide groove disposed therethrough.

5. An apparatus as claimed in claim 1 wherein said first support platform comprises a first support base.

6. An apparatus as claimed in claim 4 wherein said first adjustment mechanism comprises:

a frame;

a bracket in fixed positional alignment with respect to said frame;

a securement connecting said bracket with said connection shoulder through said at least one guide groove, said securement being dimensioned to allow movement of said connection shoulder along said guide groove;

a screw drive disposed at a first end of said bracket and engaging a first end of said connection shoulder; and a return spring disposed at a second end of said bracket and engaging a second end of said connection shoulder, said drive screw and return spring cooperating to facilitate adjustment of said first support platform along said first axis of said orthogonal axes.

7. An apparatus as claimed in claim 6 wherein said second support platform comprises a second support base, said first and second support bases engaging one another in a T-slot connection allowing said first and second support bases to move with respect to one another along said second axis of said orthogonal axes.

8. An apparatus as claimed in claim 7 wherein said second adjustment mechanism comprises:

a screw drive having a first end in generally fixed alignment with said first support platform and a second end and generally fixed alignment with said second support platform;

a bias member opposing relative movement between said first and second support platforms by said screw drive.

9. An apparatus as claimed in claim 8 wherein said T-slot connection is dovetailed.

10. An apparatus as claimed in claim 9 and further comprising one or more compressible bearings disposed at corners of said dovetailed, T-slot connection.

11. An apparatus as claimed in claim 10 wherein said one or more compressible bearings comprises hollow tubes.

12. An apparatus as claimed in claim 11 wherein said hollow tubes deform to a generally square cross-section in said dovetailed, T-slot connection.

13. An apparatus as claimed in claim 5 wherein said second support platform comprises a second support base, said first and second support bases engaging one another in a T-slot connection allowing said first and second support bases to move with respect to one another along said second axis of said orthogonal axes.

14. An apparatus as claimed in claim 13 wherein said second adjustment mechanism comprises:

a screw drive having a first end in generally fixed alignment with said first support platform and a second end and generally fixed alignment with said second support platform;

a bias member opposing relative movement between said first and second support platforms by said screw drive.

15. An apparatus as claimed in claim 13 wherein said T-slot connection is dovetailed.

16. An apparatus as claimed in claim 15 and further comprising one or more compressible bearings disposed at corners of said dovetailed, T-slot connection.

17. An apparatus as claimed in claim 16 wherein said one or more compressible bearings comprises hollow tubes.

18. An apparatus as claimed in claim 17 wherein said hollow tubes deform to a generally square cross-section in said dovetailed, T-slot connection.

19. An apparatus for adjusting the position of a sensor in a plane perpendicular to a detection axis, the apparatus comprising:

a first support platform adapted to support said sensor;

a first adjustment mechanism disposed to adjust the position of said first support platform along a first axis;

a second support platform slidably connected to said first support platform and supporting said sensor;

a second adjustment mechanism disposed to adjust the position of said second support platform with respect to said first support platform along a second axis, said first and second axes being generally orthogonal to one another and lying in a plane that is generally perpendicular to said detection axis; and at least one tube bearing positioned between said first support platform and said second support platform, the at least one tube bearing oriented parallel to the second axis such that a center tube axis defined by the at least one tube bearing extends parallel to the second axis.

20. An apparatus as claimed in claim 19 wherein the at least one tube bearing is comprised of polytetrafluoroethylene.

21. An apparatus as claimed in claim 19 wherein the at least one tube bearing has a generally non-circular cross-section.

22. An apparatus as claimed in claim 19 wherein said first support platform comprises:

a support base; and a connection shoulder extending from said support base, said connection shoulder having at least one guide groove disposed therethrough.

23. An apparatus as claimed in claim 19 wherein said first support platform comprises a first support base.

24. An apparatus as claimed in claim 23 wherein said second support platform comprises a second support base, said first and second support bases engaging one another in a T-slot connection allowing said first and second support bases to move with respect to one another along said second axis of said orthogonal axes.

25. An apparatus as claimed in claim 24 wherein said second adjustment mechanism comprises:

a screw drive having a first end in generally fixed alignment with said first support platform and a second end and generally fixed alignment with said second support platform;

a bias member opposing relative movement between said first and second support platforms by said screw drive.

26. An apparatus as claimed in claim 24 wherein said T-slot connection is dovetailed.

27. An apparatus as claimed in claim 26 wherein said at least one tube bearing is disposed at a corner of said dovetailed, T-slot connection.

28. An apparatus as claimed in claim 27 wherein said at least one tube bearing comprises one or more compressible hollow tubes.

29. An apparatus as claimed in claim 28 wherein said hollow tubes deform to a generally square cross-section in said dovetailed, T-slot connection.

30. An apparatus for adjusting the position of a sensor in a plane perpendicular to a detection axis, the apparatus comprising:

(a) a first support platform adapted to support said sensor, wherein said first support platform comprises a support base and a connection shoulder extending from said support base, said connection shoulder having at least one guide groove disposed therethrough;

(b) a first adjustment mechanism disposed to adjust the position of said first support platform, wherein said first adjustment mechanism comprises:

a frame;

a bracket in fixed positional alignment with respect to said frame;

a securement connecting said bracket with said connection shoulder through said at least one guide groove, said securement being dimensioned to allow movement of said connection shoulder along said guide groove;

a screw drive disposed at a first end of said bracket and engaging a first end of said connection shoulder; and a return spring disposed at a second end of said bracket and engaging a second end of said connection shoulder, said drive screw and return spring cooperating to facilitate adjustment of said first support platform along said first axis of said orthogonal axes;

(c) a second support platform slidably connected to said first support platform and supporting said sensor; and (d) a second adjustment mechanism disposed to adjust the position of said second support platform with respect to said first support platform along a second axis, said first and second axes being generally orthogonal to one another and lying in a plane that is generally perpendicular to said detection axis.

31. An apparatus as claimed in claim 30 wherein said second support platform comprises a second support base, said first and second support bases engaging one another in a T-slot connection allowing said first and second support bases to move with respect to one another along said second axis of said orthogonal axes.

32. An apparatus as claimed in claim 31 wherein said second adjustment mechanism comprises:

a screw drive having a first end in generally fixed alignment with said first support platform and a second end and generally fixed alignment with said second support platform;

a bias member opposing relative movement between said first and second support platforms by said screw drive.

33. An apparatus as claimed in claim 32 wherein said T-slot connection is dovetailed.

34. An apparatus as claimed in claim 33 and further comprising one or more compressible bearings disposed at corners of said dovetailed, T-slot connection.

35. An apparatus as claimed in claim 34 wherein said one or more compressible bearings comprises hollow tubes.

36. An apparatus as claimed in claim 35 wherein said hollow tubes deform to a generally square cross-section in said dovetailed, T-slot connection.

37. A flow cytometer comprising:

(a) an emitter adapted to emit a beam of electromagnetic radiation;

(b) a sensor adapted to detect electromagnetic radiation traveling along a detection axis;

(c) a flow cell disposed between said emitter and said sensor; and (d) a sensor alignment unit supporting said sensor for detection of said electromagnetic radiation traveling along said detection axis, said sensor alignment unit adapted to allow adjustment of the position of said sensor along orthogonal axes lying in a plane that is generally perpendicular to said detection axis, wherein said sensor alignment unit comprises:

a first support platform;

a first adjustment mechanism disposed to adjust the position of said first support platform along a first axis of said orthogonal axes;

a second support platform connected to said first support platform and supporting said sensor;

a second adjustment mechanism disposed to adjust the position of said second support platform with respect to said first support platform along a second axis of said orthogonal axes.

38. An apparatus as claimed in claim 37 wherein said first support platform comprises:

a support base; and a connection shoulder extending from said support base, said connection shoulder having at least one guide groove disposed therethrough.

39. An apparatus as claimed in claim 38 wherein said first adjustment mechanism comprises:

a frame;

a bracket in fixed positional alignment with respect to said frame;

a securement connecting said bracket with said connection shoulder through said at least one guide groove, said securement being dimensioned to allow movement of said connection shoulder along said guide groove;

a screw drive disposed at a first end of said bracket and engaging a first end of said connection shoulder; and a return spring disposed at a second end of said bracket and engaging a second end of said connection shoulder, said drive screw and return spring cooperating to facilitate adjustment of said first support platform along said first axis of said orthogonal axes.

40. An apparatus as claimed in claim 37 wherein said first support platform comprises a first support base.

41. An apparatus as claimed in claim 40 wherein said second support platform comprises a second support base, said first and second support bases engaging one another in a T-slot connection allowing said first and second support bases to move with respect to one another along said second axis of said orthogonal axes.

42. An apparatus as claimed in claim 41 wherein said second adjustment mechanism comprises:

a screw drive having a first end in generally fixed alignment with said first support platform and a second end in generally fixed alignment with said second support platform;

a bias member opposing relative movement between said first and second support platforms by said screw drive.

43. In a flow cytometer having an emitter adapted to generate a beam of electromagnetic radiation toward a particle chamber disposed in a path of said beam of electromagnetic radiation and a sensor adapted to detect electromagnetic radiation along a detection axis, a method for optimizing the position of the sensor with respect to the detection axis comprising the steps of:

monitoring an electronic signal corresponding to the output of said sensor;

adjusting the position of said sensor along at least two orthogonal axes lying in a plane perpendicular to said detection axis until said electronic signal meets one or more predetermined criteria, wherein the step of adjusting the position of said sensor comprises adjusting a first support platform along a first one of said at least two orthogonal axes, and adjusting a second support platform connected to said first support platform along a second one of said at least two orthogonal axes.

44. A method as claimed in claim 43 wherein said monitoring step comprises visually monitoring said electronic signal using an oscilloscope.

45. A method as claimed in claim 43 wherein said adjusting step comprises the steps of:

adjusting the position of said sensor along the first one of said at least two orthogonal axes using a first adjustment mechanism; and adjusting the position of said sensor along the second one of said at least two orthogonal axes using a second adjustment mechanism.

46. A method as claimed in claim 44 wherein said adjusting step comprises adjusting the position of said sensor along said at least two orthogonal axes lying until the magnitude of said electronic signal is maximized.

47. A method as claimed in claim 44 wherein said adjusting step comprises adjusting the position of said sensor along said at least two orthogonal axes until the magnitude of a peak pulse of said electronic signal is maximized.

48. A method as claimed in claim 44 wherein said adjusting step comprises adjusting the position of said sensor along said at least two orthogonal axes until the magnitude of a peak null of said electronic signal is maximized.

* * * * *